United States Patent [19]

Ehmann

[11] 4,160,786

[45] Jul. 10, 1979

[54] PROCESS FOR ISOMERIZING CYCLOALKENOL TO CYCLOALKANONE

[75] Inventor: William J. Ehmann, Orange Park, Fla.

[73] Assignee: SCM Corporation, New York, N.Y.

[21] Appl. No.: 933,058

[22] Filed: Aug. 11, 1978

[51] Int. Cl.$^2$ .................... C07C 45/00; C07C 45/16
[52] U.S. Cl. .................... 260/586 P; 260/586 R
[58] Field of Search .................... 260/586 P

[56] References Cited

U.S. PATENT DOCUMENTS

| | | | |
|---|---|---|---|
| 2,052,736 | 9/1936 | Zimmerli | 260/586 P |
| 2,087,691 | 7/1937 | Lazier | 260/586 P |
| 2,163,284 | 6/1939 | Lazier | 260/586 P |
| 2,218,457 | 10/1940 | Winans | 260/586 P |
| 2,462,712 | 2/1949 | Barney | 260/586 P |
| 2,831,028 | 4/1958 | Bain et al. | 260/586 P |
| 2,894,040 | 7/1959 | Bain et al. | 260/586 P |
| 3,014,047 | 12/1961 | Bain et al. | 260/586 P |
| 3,014,080 | 12/1961 | Bain et al. | 260/586 P |
| 3,405,185 | 10/1968 | Houlihan et al. | 260/586 P |
| 3,422,146 | 1/1969 | Defoor | 260/586 P |
| 3,647,880 | 3/1972 | Blumenthal | 260/586 P |
| 4,020,108 | 4/1977 | Ehmann | 260/586 P |
| 4,025,562 | 5/1977 | Verbrugge et al. | 260/586 P |

*Primary Examiner*—Norman Morgenstern
*Attorney, Agent, or Firm*—Merton H. Douthitt

[57] ABSTRACT

A beta-, gamma-unsaturated cycloalkenol contaminated with an acid-forming moiety is catalytically isomerized to a cycloalkanone in the presence of copper chromite catalyst and an insoluble base which suppresses the acid-forming moiety during the isomerization.

12 Claims, No Drawings

PROCESS FOR ISOMERIZING CYCLOALKENOL TO CYCLOALKANONE

BACKGROUND OF THE INVENTION

The present invention relates to the catalytic isomerization of allylic alcohols to saturated ketones and more particularly to the catalyzed isomerization of a beta-, gamma-unsaturated cycloalkenol to a saturated cycloalkanone.

In pure form, the instant cycloalkenols can be readily isomerized with copper chromite to their corresponding saturated cycloalkanones. However, various methods of making the cycloalkenols have residual acid-forming moieties contaminating the cycloalkenol. For example, one convenient method of preparing a cycloalkenol is described in U.S. Pat. No. 3,076,839. Normally, this process will leave impurities including organic halides and carboxylic acid esters. Such impurities can react under the influence of heat or isomerization catalysts to generate acids such as carboxylic acids, mineral acid, or Lewis acids. Such acidic moieties, even in trace amounts, can cause dehydration or isomerization of the alkenols under isomerization conditions, thereby substantially reducing the yield of the desired cycloalkanone.

The instant invention provides a method for suppressing the adverse effects which the acid-forming moiety contaminating the cycloalkenol would otherwise display during the isomerization process. In a preferred embodiment of the present invention, the instant isomerization process is an important step in a new synthesis of dl-method.

BROAD STATEMENT OF THE INVENTION

The instant invention is a process for isomerizing a beta-, gamma-unsaturated cycloalkenol to a cycloalkanone under isomerization conditions wherein the cycloalkanone is contaminated with an acid-forming moiety capable of causing dehydration of said cycloalkenol. The process comprises forming a reaction mixture of said cycloalkenol, of catalytic amount of copper chromite catalyst, and between about 0.01% and about 10% by weight of said cycloalkenol of an insoluble base which renders the moiety substantially incapable of causing dehydration in the process. The reaction mixture is heated at about 150° to about 300° C. for a time sufficient for the cycloalkanone to be formed. The resulting cycloalkanone product then is separated from the reaction mixture.

DETAILED DESCRIPTION OF THE INVENTION

Work on the present invention revealed that use of a base which is even moderately soluble in low concentration in the cycloalkenol enhances a competing reaction, dehydrogenation of the cycloalkenol to an alpha-, beta-unsaturated cycloalkenone. At higher concentrations, such soluble base inhibits both isomerization and dehydrogenation of the feed cycloalkenol. Thus, the preferred bases for the present invention are insoluble in the cycloalkenol, including not being solvated by nor ionized in the cycloalkenol. For present purposes a base will be insoluble in the cycloalkenol if its solubility under the reaction conditions does not substantially exceed about 5 mmoles (millimoles) per gram of catalyst used, and preferably not more than about 1 mmole per gram of catalyst. It is recognized that the effect of slightly soluble bases can be approximated by employing trace amounts of a soluble base.

Suitable insoluble bases for use in the present process include, but are not limited to, Group IA and Group IIA carbonates and bicarbonates, and Group IIA oxides and hydroxides. For purposes of this application, Group IA metals include lithium, sodium, potassium, rubidium, and cesium; and Group IIA metals include magnesium, calcium, strontium, and barium. For economy, sodium carbonate is preferred in the present process as the insoluble base, though sodium bicarbonate, potassium carbonate, and potassium bicarbonate are quite useful also. The proportion of insoluble base should be adjusted to at least fully neutralize the acid-forming moieties contaminating the feed cycloalkenol and preferably an excess beyond this will be used. The proportion of acid-forming moiety typically found in the feed cycloalkenol will range more often from about 5 to 1000 ppm by weight of the cycloalkenol. Broadly then, the insoluble base should be present in the feed cycloalkenol in a proportion ranging between about 0.001 to about 10% by weight of the cycloalkenol and preferably between about 0.1 and 5% by weight.

The copper chromite catalyst can be provided in supported or unsupported form though the supported form decidedly is preferred. The support material can be conventional such as, for example, various aluminas, silica gel, activated carbon, and the like. The copper chromite catalyst can be stabilized with an alkaline earth metal oxide, such as barium oxide or calcium oxide, or with a multivalent metal oxide, such as manganese oxide, although this is not essential. Typically, the oxide stabilizing material ranges from about 4% to 8% by weight of the catalyst. The molar ratio of the copper to chromite components in the catalyst is not critical and such components can be in typical amounts as heretofore conventionally used in the art. Typically, the molar ratio of such components is about 1:1. The copper chromite catalyst generally ranges between about 0.1 and about 10% by weight of the cycloalkenol fed to the process and preferably between about 0.5 and 5%.

Reaction conditions for the present process include temperatures of about 150° to about 300° C., desirably between about 180° and 300° C., and preferably between about 180° and 250° C. Preferably, atmospheric pressure is used, though subatmospheric or superatmospheric pressure may be desirable upon occasion. The product cycloalkanone generally is formed after about 0.25 to 2 hours reaction time.

Suitable beta-, gamma-unsaturated cycloalkenols for the present process include menthenols selected from the group consisting of para-menth-1-ene-3-ol, para-menth-3-ene-2-ol, para-menth-3-ene-5-ol, para-menth-1-ene-6-ol, para-mentha-1,8-dien-6-ol, and mixtures thereof. This invention can be especially valuable when it is applied to mixtures of cycloalkenols. These mixtures often occur when the cycloalkenol is derived from a cyclodiene. For example, hydration of menthadienes as described in U.S. Pat. No. 3,076,839 can produce a mixture of menthenols, piperitols, dihydrocarveols, carvenols and alpha-terpineol. This mixture is not separable conveniently by conventional methods such as distillation. Subjecting this mixture to the present invention results in the formation of a mixture containing menthone, isomenthone, carvomenthone, and alpha-terpineol, which products are easily separable, for example, by distillation. Such separated products then can be converted to other valuable products such as, for example, menthol.

Another valuable feature of the present invention is the substantial retention of optical activity in the product cycloalkanones. For example, menthone produced from cis-piperitol by the present invention retains over 80% of the original optical activity of the optically active menthone fed to the present process.

One method for improving the overall yield of product menthone and carvomenthone made by the process involves the hydrogenation of by-product carvenone and piperitone to carvomenthone and menthone. This hydrogenation may be done prior to or after separation of the isomerization products. Such hydrogenation can be conducted in conventional fashion utilizing a nickel hydrogenation catalyst, such as Raney nickel, or a similar hydrogenation catalyst used in the art. Hydrogenation conditions comprehend temperatures of about 0° to 300° and pressures of about 0 to 1000 psi.

It should be noted that another preferred cycloalkenol which can be fed to the instant process is carveol which can be isomerized to dihydrocarvone. Dihydrocarvone is especially prized for use in perfumery and flavoring.

The following examples show how the instant invention can be practiced but should not be construed as limited. In this application, all degrees are in degrees Centigrade and all percentages are weight percentages unless otherwise expressly indicated.

EXAMPLES 1-6

These examples illustrate the improved yield realized in the isomerization of piperitols in the presence of an insoluble base.

In all reactions, 25 g of piperitol containing 76.8% cis-piperitol, 17.2% trans-piperitol, and 56 ppm of chloride (acid-forming moiety) were added to the catalyst and heated to reflux for 3 hours. The product then was cooled, filtered, and analyzed by GLPC. "Conversion" figures represent the amount of feed piperitol consumed during the isomerization reaction expressed in weight-percent. "Yield" figures represent the amount of cycloketone products formed during the reaction expressed as a weight-percent of the piperitols consumed during the reaction. The cycloketone products are considered to be menthone and isomenthone, which are interconverted under the reaction conditions, and piperitone which can be converted to menthone via conventional techniques, eg. hydrogenation. Results are reported in Table I.

TABLE I

| Example | Catalyst | Conversion | Yield of Menthone/Isomenthone Piperitone |
|---|---|---|---|
| 1 | 1% G-15 | 74.0% | 2.1% |
| 2 | 1% G-22 | 34.0% | 28.3% |
| 3 | 1% G-89 | 45.6% | 5.5% |
| 4 | 1% G-15 .5% Na2CO3 | 64.0% | 94.7% |
| 5 | 1% G-22 .5% Na2CO3 | 82.6% | 92.19 |
| 6 | 1% G-89 .5% Na2CO3 | 82.5% | 87.3% |

G-15 - Girdler G-15 Copper Chromite Catalyst
G-22 - Girdler G-22 Barium promoted copper chromite catalyst (11-½% barium oxide)
G-89 - Girdler G-89 Manganese promoted copper chromite catalyst (3% manganese oxide)
All catalysts are supplied by Girdler Chemical, Inc., Louisville, Kentucky 40201.

The foregoing tabled results demonstrate that the addition of an insoluble base to the reaction mixture effectively improves the conversion of feed piperitols and improves the yield of the desired cycloketones from the piperitols consumed during the isomerization reaction. Without the presence of the insoluble base, the chloride acid-forming moiety displays a substantial deleterious effect on the isomerization reaction.

EXAMPLES 7-13

Examples 7-13 compare the use of an insoluble base such as sodium carbonate or sodium bicarbonate, a slightly soluble base such as sodium acetate, and various amounts of soluble bases such as potassium stearate and potassium hydroxide.

In all reactions, 25 g of cis-piperitol containing about 20 ppm of chloride was added to 0.5 g of the Girdler G-22 barium promoted copper chromite catalyst and base. This reaction mixture was heated to reflux for 1 hour. After cooling and filtering, the product was analyzed by GLPC. Results of these experiments are displayed in Table II.

TABLE II

| Exper. | Base | Menthone/ Isomenthone | Piperitone | cis-Piperitol |
|---|---|---|---|---|
| 7 | 2% Na2CO3 | 85.6% | 11.0% | — |
| 8 | 2% NaHCO3 | 84.5% | 8.9% | — |
| 9 | 2% NaOAc | 26.7% | 61.3% | — |
| 10* | 2% Potassium | 21.0% | 41.3% | 21.7% |
| 12 | .5% KOH | No Reaction Detected | | |
| 13 | .1% KOH | 34.1% | 60.0% | 1.09% |

*Reaction time 4 hours

The effectiveness of an insoluble base in the reaction is shown in Examples 7 and 8. The use of the slightly soluble base potassium stearate in Example 9 substantially lowers the yield of menthone/isomenthone products and results in a substantial proportion of the feed cis-piperitol not being consumed during the reaction. At lower levels of potassium stearate in Example 11, improved yields can be seen, though the amount of piperitone formed by the competing dehydrogenation reaction still is quite substantial. The results of Example 12 show total inhibition of any reaction at high levels of the very soluble base KOH. At lower levels of KOH in Example 13, dehydrogenation is the predominant reaction rather than the desired isomerization reaction.

EXAMPLE 14

A pressure vessel was charged with 500 g of a mixture of alcohols containing 93.9 g of cis-piperitol, 136.45 g of trans-piperitol, and 187.,8 g of cis and trans-carvenols, 10 g of Girdler G-22 barium promoted copper chromite catalyst, and 10 g of sodium carbonate. The vessel was heated with stirring to 200°-240° C. for 2 hours. After cooling, the product was filtered and distilled to yield 210.5 g of menthone/isomenthone mixture and 147.3 g of carvomenthone. The menthones and carvomenthones were cleanly separated by distillation. The distillation residue containing piperitone and carvenone was hydrogenated at 60 psig hydrogen pressure and ambient temperature using 2% Raney nickel catalyst. Distillation of the hydrogenated product yielded an additional 8.2 g of mentone and 5.3 g of carvomenthone.

EXAMPLE 15

A flask was charged with 2.0 g of Girdler G-22 barium promoted copper chromite catalyst, 1.0 g of sodium carbonate, and 100 g of (4R)-piperitol (47.5% 3S and 48.9% 3R). The mixture was heated slowly with stirring to 215° and held at this temperature for 1 hour. After cooling an filtering, the product was analyzed by GLPC to contain 43.9% menthone, 25.9% isomenthone, and 23.3% piperitone. The menthone and isomenthone were recovered by distillation and converted to the enol acetate by the method of Yoshida et al (T. Yoshida, A. Komatsu, and M. Indo, *Agr. Biol. Chem.*, 27, 433 (1963)).

Measurement of the optical rotation of enol acetate showed that there was an 81% enantiomeric excess of the R-configuration at the 1-carbon atom in the enol acetate and by inference in the menthone/isomenthone mixture.

I claim:

1. A process for isomerizing a beta-, gamma-unsaturated cycloalkenol to a cycloalkanone, wherein said cycloalkenol is contaminated with an acid-forming moiety capable of causing dehydration of said cycloalkenol, which comprises:

forming a reaction mixture of said cycloalkenol, a catalytic amount of copper chromite catalyst, and between about 0.01% and 10% by weight of said cycloalkenol of a base which has a solubility in said reaction mixture not substantially above about 5 millimoles per gram of said catalyst, said base rendering said moiety substantially incapable of causing said dehydration, heating said reaction mixture at about 150° to 300° C. until said cycloalkanone is formed; and recovering said cycloalkanone from said reaction mixture.

2. The process of claim 1 wherein said reaction mixture is heated at about 180° to 300° C.

3. The process of claim 1 wherein said base has a solubility in said reaction mixture of not above about 1 millimole per gram of said catalyst.

4. The process of claim 1 wherein acid-forming moiety comprises an organic halide and/or a carboxylic acid ester.

5. The process of claim 1 wherein said moiety ranges between about 5 and 1,000 ppm by weight of said cycloalkenol.

6. The process of claim 5 wherein the proportion of said base is between about 0.001 and about 10% by weight of said cycloalkenol.

7. The process of claim 1 wherein said catalyst ranges between about 0.1 and 10% by weight of said cycloalkenol.

8. The process of claim 1 wherein said base is selected from a Group IA or Group IIA carbonate or bicarbonate, and a Group IIA oxide or hydroxide.

9. The process of claim 8 wherein said base is selected from sodium carbonate, sodium bicarbonate, potassium carbonate, and potassium bicarbonate.

10. The process of claim 1 wherein said cycloalkenol is selected from para-menth-1-ene-3-ol, para-menth-3-ene-2-ol, para-menth-3-ene-5-ol, para-menth-1-ene-6-ol, para-mentha-1,8-dien-6-ol, and mixtures thereof.

11. The process of claim 1 wherein said cycloalkenol is (4R)-piperitol and said cycloalkanone recovered is (1R)-menthone/isomenthone.

12. The process of claim 1 wherein said cycloalkenol is (4S)-piperitol and said cycloaklenone recovered is (1S)-menthone/isomenthone.

* * * * *

UNITED STATES PATENT AND TRADEMARK OFFICE
CERTIFICATE OF CORRECTION

PATENT NO. : 4,160,786
DATED : July 10, 1979
INVENTOR(S) : William J. Ehmann

It is certified that error appears in the above-identified patent and that said Letters Patent are hereby corrected as shown below:

Column 1, line 14, change "have" to --leave--; line 33, change "method" to --menthol--; line 42, change "of catalytic" to --a catalytic--; column 4, line 31, in the Table, fourth line of the second column, change "2% Potassium" to --2% Potassium Stearate--.

Signed and Sealed this

Twenty-third Day of October 1979

[SEAL]

Attest:

RUTH C. MASON
*Attesting Officer*

LUTRELLE F. PARKER
*Acting Commissioner of Patents and Trademarks*